United States Patent
Coates

[11] Patent Number: 5,891,122
[45] Date of Patent: Apr. 6, 1999

[54] TAILORED AND PROTECTIVE UNDERGARMENTS

[75] Inventor: Fredrica Coates, Earlysville, Va.

[73] Assignee: Tailored Technologies, Inc., Earlysville, Va.

[21] Appl. No.: 627,338

[22] Filed: Apr. 4, 1996

Related U.S. Application Data

[63] Continuation of Ser. No. 303,043, Sep. 8, 1994, abandoned, which is a continuation-in-part of Ser. No. 207,485, Mar. 7, 1994, abandoned.

[51] Int. Cl.⁶ ........................................... A61F 13/15
[52] U.S. Cl. ............................ 604/385.1; 604/385.2; 604/393
[58] Field of Search ...................... 604/358, 385.1, 604/385.2, 399, 378, 393

[56] References Cited

U.S. PATENT DOCUMENTS

| | | |
|---|---|---|
| Re. 28,483 | 7/1975 | Ralph . |
| 731,201 | 6/1903 | Miller et al. . |
| 1,989,283 | 1/1935 | Limacher . |
| 2,545,761 | 3/1951 | Brink . |
| 2,558,215 | 6/1951 | Habig et al. . |
| 2,571,577 | 10/1951 | Howard . |
| 2,684,677 | 7/1954 | Pinney . |
| 2,743,725 | 5/1956 | Mathews . |
| 3,349,769 | 10/1967 | Piekarski . |
| 3,383,693 | 5/1968 | Kahn et al. . |
| 3,386,443 | 6/1968 | Goldstein . |
| 3,563,242 | 2/1971 | Hedstrom . |
| 3,568,676 | 3/1971 | Guercio . |
| 3,653,381 | 4/1972 | Warnken . |
| 3,742,953 | 7/1973 | Lee . |
| 3,955,575 | 5/1976 | Okuda . |
| 4,020,843 | 5/1977 | Kandall . |
| 4,315,508 | 2/1982 | Bolick . |
| 4,425,128 | 1/1984 | Motomura . |
| 4,475,912 | 10/1984 | Coates . |
| 4,537,591 | 8/1985 | Coates . |
| 4,578,073 | 3/1986 | Dysart et al. . |
| 4,680,030 | 7/1987 | Coates et al. . |
| 4,681,581 | 7/1987 | Coates . |
| 4,695,278 | 9/1987 | Lawson . |
| 4,704,117 | 11/1987 | Mitchell . |
| 4,728,326 | 3/1988 | Gilles . |
| 4,747,846 | 5/1988 | Boland et al. . |
| 4,773,906 | 9/1988 | Krushel . |
| 4,801,298 | 1/1989 | Sorenson et al. . |
| 4,808,177 | 2/1989 | DesMarais et al. . |

(List continued on next page.)

FOREIGN PATENT DOCUMENTS 0 475 702  3/1992  European Pat. Off. .

*Primary Examiner*—Michael J. Milano
*Assistant Examiner*—Dennis Ruhl
*Attorney, Agent, or Firm*—McDermott, Will & Emery

[57] ABSTRACT

A tailored diaper or diaper cover is constructed of a waterproof diaper shell enclosing an elongated sling of waterproof or non-waterproof material having its upper and lower ends attached to, and its opposite sides free and floating on, the shell. A fluid absorbent pad on the inner surface of the sling is circumscribed by the waterproof material of the sling so as to establish a channel to entrap and isolate fluid from the shell. The lines of attachment between the waterproof and fluid absorbent materials at the upper and lower ends of the sling are arcuate, and the periphery of the sling is covered by elastic trim, causing the sling and pad to cup the pubis of a user when the diaper is worn. Entrapment of fluid within the sling may be enhanced by different pad inserts. A washable pad of novel "butterfly" construction within the diaper or diaper cover enhances fluid absorption and drying. Another aspect of this invention provides embodiments of a tailored urinal for men, having a novel fluid containment bag and adapted to reside within underwear. Another aspect of this invention involves a new tab construction and manufacturing procedure whereby the periphery of the finished fastening tab in emcompassed by soft threads produced by an overlooking machine. Another aspect of the invention is a diaper cover containing a simple leakproof inner sling which holds a pad by folded frontal edges of the sling.

12 Claims, 10 Drawing Sheets

U.S. PATENT DOCUMENTS

| | | |
|---|---|---|
| 4,850,987 | 7/1989 | Gilomen . |
| 4,869,724 | 9/1989 | Scripps ................................. 604/389 |
| 4,904,251 | 2/1990 | Igaue et al. . |
| 4,961,736 | 10/1990 | McCloud ........................... 604/385.1 |
| 4,994,037 | 2/1991 | Bernardin . |
| 5,009,649 | 4/1991 | Goulter et al. . |
| 5,015,251 | 5/1991 | Cherubini ............................. 606/203 |
| 5,069,572 | 12/1991 | Wippler et al. . |
| 5,074,853 | 12/1991 | Bryant . |
| 5,106,382 | 4/1992 | Henry . |
| 5,112,324 | 5/1992 | Wallace . |
| 5,112,326 | 5/1992 | Quadrini . |
| 5,137,526 | 8/1992 | Coates ................................... 604/391 |
| 5,167,653 | 12/1992 | Igaue et al. . |
| 5,176,671 | 1/1993 | Roessler et al. ...................... 604/391 |
| 5,200,245 | 4/1993 | Brodrick, Jr. ......................... 428/100 |
| 5,205,298 | 4/1993 | Hurst . |
| 5,209,743 | 5/1993 | Hardison . |
| 5,217,447 | 6/1993 | Gagnon . |
| 5,246,431 | 9/1993 | Minetola et al. . |
| 5,368,585 | 11/1994 | Dokken . |

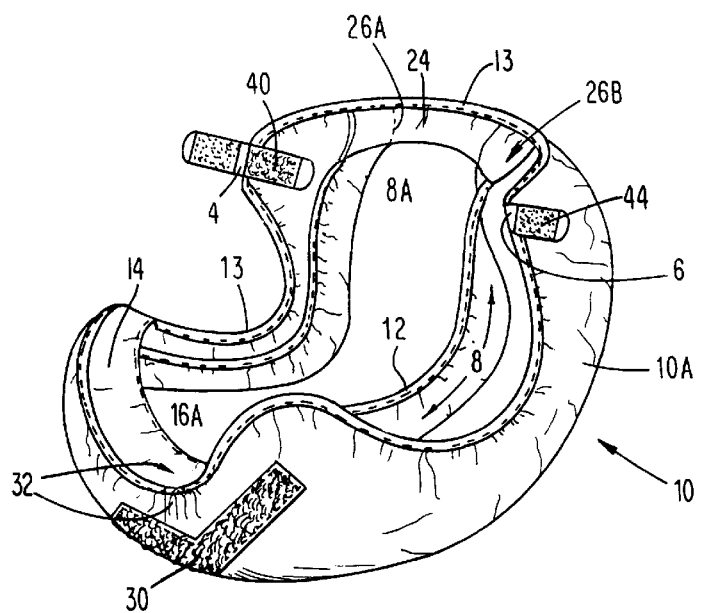
Figure 1
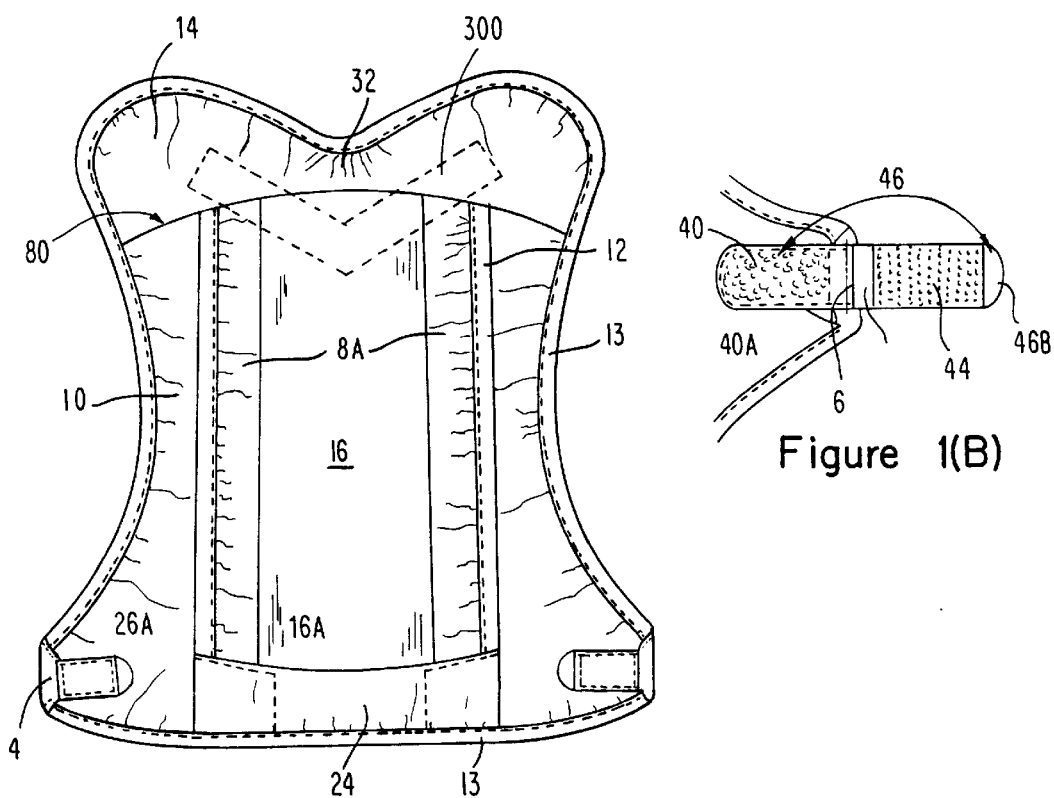
Figure 1(A)
Figure 1(B)

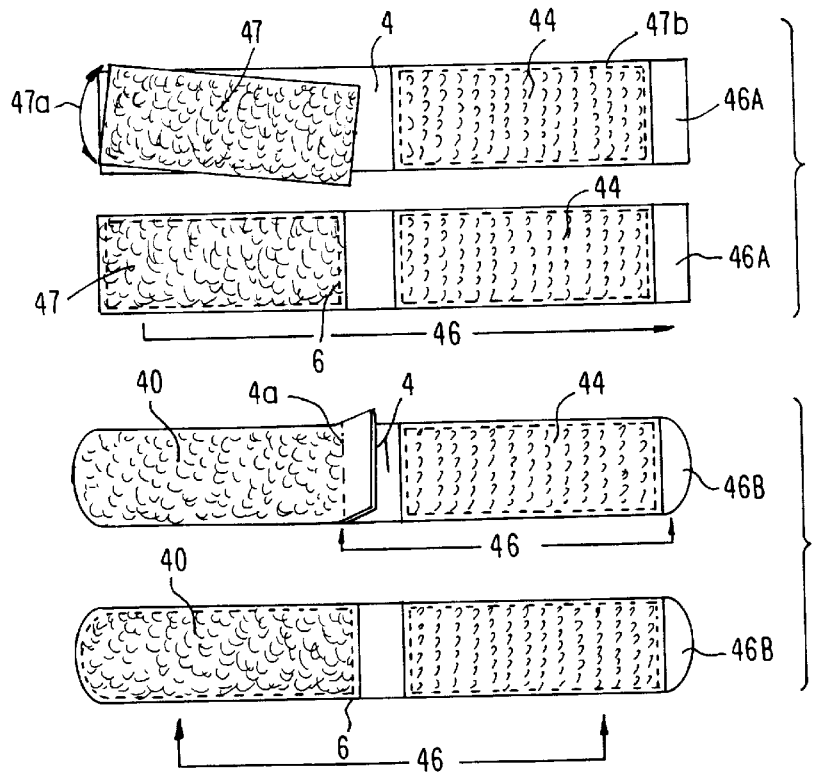
Figure 3(A)
Figure 3(B)
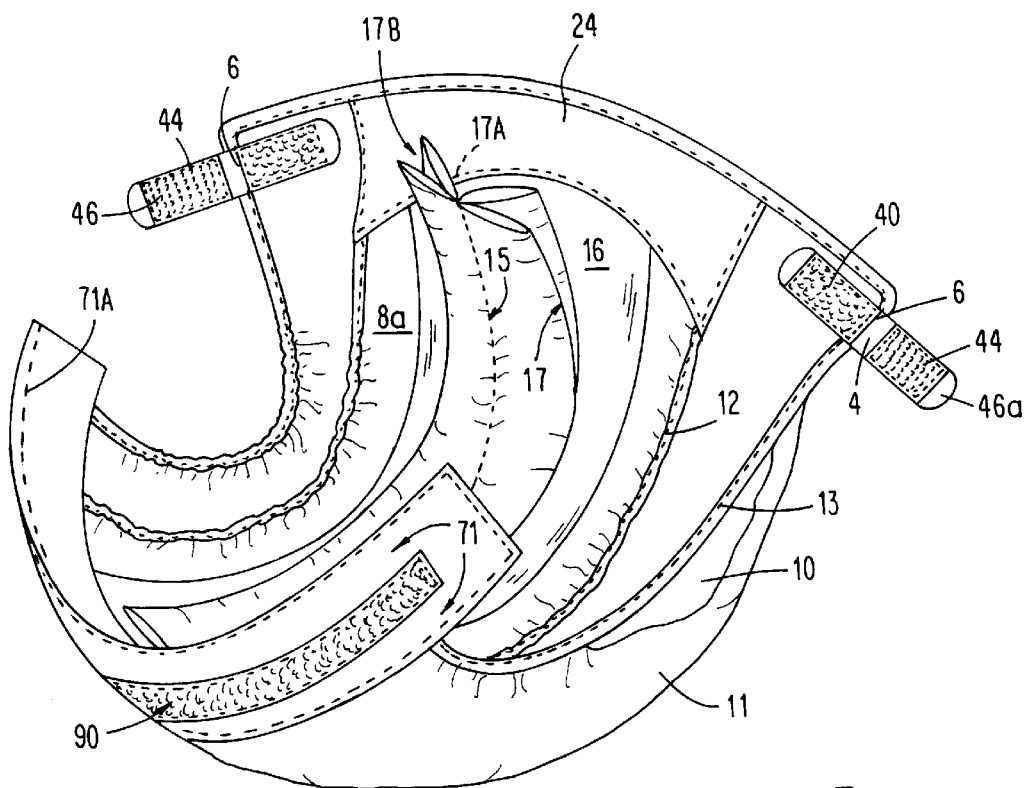
Figure 3

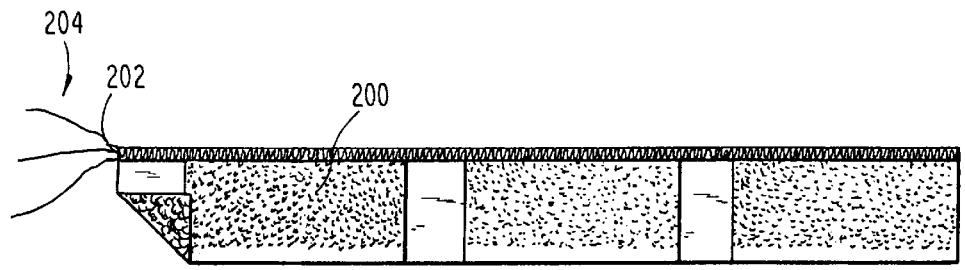
Figure 12
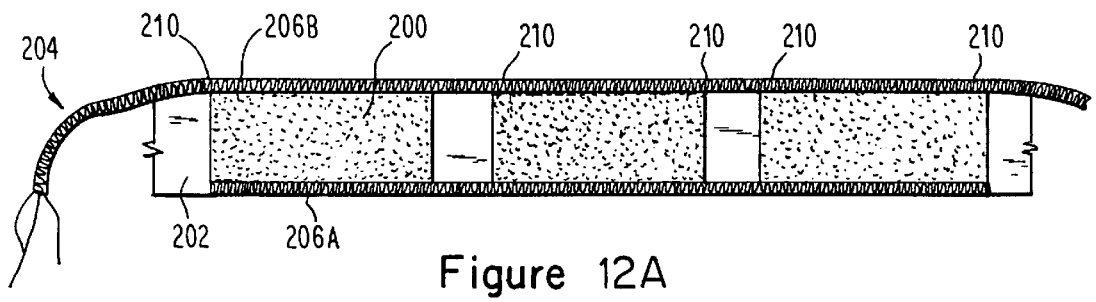
Figure 12A
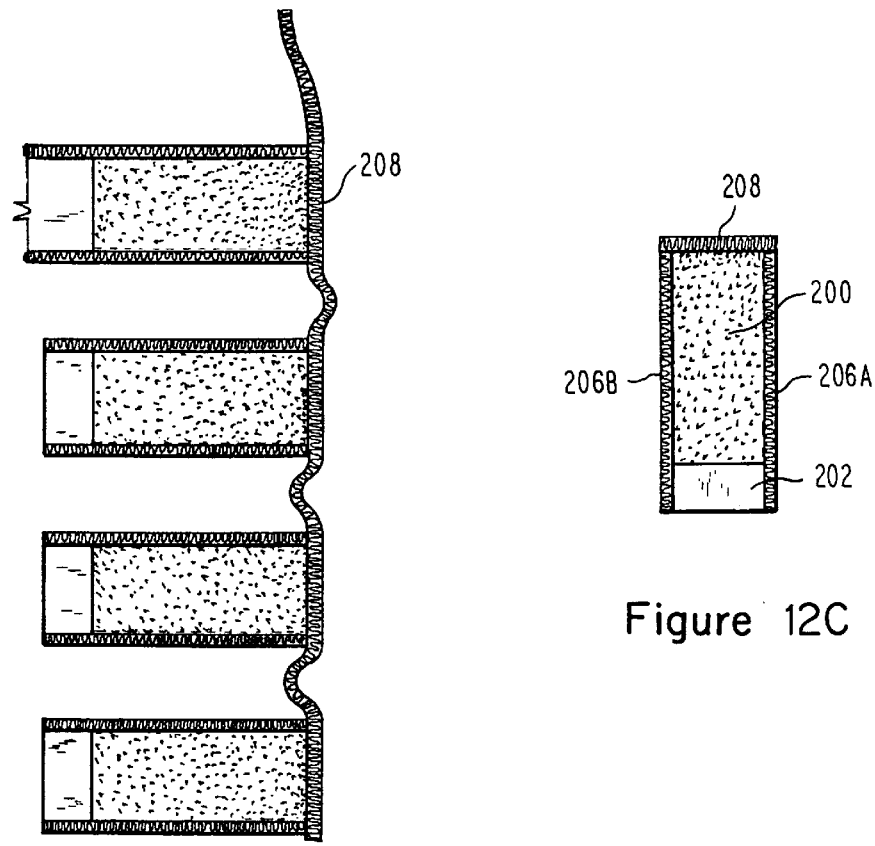
Figure 12C
Figure 12B

TAILORED AND PROTECTIVE UNDERGARMENTS

REFERENCE TO RELATED APPLICATIONS

This application is a continuation of application Ser. No. 08/303,043, filed Sep. 8, 1994, now abandoned, which is a continuation-in-part of application Ser. No. 08/207,485, filed Mar. 7, 1994, now abandoned.

TECHNICAL FIELD

This invention relates generally to the field of protective undergarments, such as adult and infant diapers, protective underwear and urinals, and more particularly to novel reusable or disposable fluid containment structures and manufacturing methods therefor.

BACKGROUND ART

Disposable diapers are in widespread use throughout the country as a result of the convenience in using them. However, the fluid absorbing characteristics of disposable diapers, particularly at the legholes, is insufficient. Disposable diapers are not tailored, and the appearance of disposable diapers is not appealing to most adult users. Hence, one aspect of this invention is in applying significant enhancements to the field of disposable diapers and methods of producing them.

However, disposable diapers burden our ecology, contributing substantially to waste that must be processed by municipalities. Despite the convenience of disposability, there is a need to return to less waste producing undergarment systems both for infant and adult use domestically and institutionally. I am not aware of any existing technology combining elements of disposable and reusable undergarment systems in a practical and appealing manner to produce tailored undergarments that are comfortable, effective and cost efficient as well as environmentally appropriate.

Recent prior art has produced many significant advances in the field of reusable adult and infant diapers. In my U.S. Pat. No. 4,475,912, issued on Oct. 4, 1984, a cloth diaper is configured to "grow" with an infant from birth to toddler, through unique placement of filamentary-type fasteners and folding of fabric upon which the fasteners are sewn. Recognizing the tendency of the hook-type material within filamentary fasteners to accumulate with lint, and become unusable following washings, my U.S. Pat. No. 4,537,591 is directed to an improvement on hook and loop fasteners for cloth diapers, incorporating a protective cover to selfclose filamentary fasteners during washing. My U.S. Pat. No. 4,681,581, issued on Jul. 25, 1987, discloses various embodiments for fastening diapers, reducing the cost of manufacturing. In U.S. Pat. No. 4,680,030, issued on Jul. 14, 1987, various configurations of hook and loop filamentary fasteners, arranged on fabric flaps of material, enable the diapers to withstand institutional washing conditions, high temperatures and chemicals. My U.S. Pat. No. 5,137,526, issued on Aug. 11, 1992, is directed to methods of diaper construction such that fluids issuing from the wearer's pubis area are contained and encased within the diaper. This patent also describes improved methods of construction presenting the diaper with a more finished appearance while reducing costs. My co-pending application Ser. No. 08/104,700, filed on Aug. 11, 1993, teaches a novel construction of "sling" portions of reusable diapers for retaining fluid absorbent pads to the pubis.

The present invention represents improvement upon my previously developed technology to more effectively fit the wearer and isolate the wearer's legs, encasing fluid to just the wearer's pubis area and away from the legs, pelvis area, clothing and surrounding bedding. An aspect of this invention also represents evolution of this new technology to encompass tailored slings and urinals, that is, vessels for containing the passage of fluid from a bedridden or mobile individual. Such vessels have previously been served by relatively cumbersome garment devices, disposable bedpads, and bedpans made of rubber, metal or plastic materials.

Hard rubber, metal or plastic urinals are unable to conform to the shape of the body, and spilling is inevitable. Hence, these bedpans allow the spread of moisture to the rest of the body. Spreading of moisture occurs quickly, making the patient feel uncomfortable and creating considerable extra work for his or her caretaker.

Garment-type urinals, like typical cloth diapers, are somewhat ineffective as a result of leakage through the legholes where most of the fluid escapes to the bed and clothing. Perhaps the only efficient urinals of which I am aware are the fitted condom-type rubber or bag-type devices designed for men. But even these are difficult to attach to the male so that fluid is drained off, a process usually involving clumsy tubes running from the receptacle into a larger receptacle for emptying. If the urinal is hand-held, a skillful caretaker is required or spilling is inevitable. This process can be embarrassing and uncomfortable for the male wearer.

Goulter, U.S. Pat. No. 5,009,649, Hurst, U.S. Pat. No. 5,205,298, Wallace, U.S. Pat. No. 5,112,324, Bryant, U.S. Pat. No. 5,074,853, Lee, U.S. Pat. No. 3,742,953 and Pouch, U.S. Pat. No. 824,634 disclose urinals fitted to the male anatomy. However, these urinals are not tailored to a garment or effective to prevent leaking. The urinals additionally are not easily handled by the user caring for himself.

Recently, there have been substantial changes in disposable diaper technology by implementing the use of chemical gels placed in the central portion of those diapers. When technology of this nature is used, the remainder of the disposable diaper does not become wet, for the gelling action is so efficient it consolidates the fluid to a small localized area between the legs. Disposable pad inserts carrying the gel material are also available, examples being marketed under the brand name "Fitti" or "Diaper Doubler." When chemical gels are placed in an insert for absorption, the remainder of the disposable diaper in effect becomes useless and uncomfortable. Furthermore, the portion of the garment carrying the gel tends to slip about. I am not aware of any technology incorporating these disposable pad inserts within tailored vessels for securing of the pads against the pubis for an absolutely stationary and secure fit without slipping.

Sanitary napkins have been provided within panties, but these napkins, or disposable pads, are generally backed with plastic and adhesive. It is commonly known that an imperfect fit results, and pads do not stay in place, with or without an adhesive. Pads that slip in panties, whether used for absorbing urine or blood, cause devastating accidents and embarrassment for the wearer. This slipping of the pad usually is due to an excessive amount of movement in that area of the body where the legs attach to the pubis area. Hence the pull or motion of the legs dislodges the pad.

In the prior art, reusable pads are retained in and attached to garments, but without tailoring to fit human anatomy. To stabilize pad movement, conventional pockets such as disclosed in Wippler, U.S. Pat. No. 5,069,692 have been taught. The pocket placed in the rear or any portion of the garment represents high risk for entrapping feces, creating difficulty in cleaning.

Furthermore, because reusable pads do not contain gel, they must be relatively thick to absorb sufficient fluid for heavy use. These pads, however, are not easily cleaned, and drying requires a considerable amount of time and consumption of energy. The thicker the pad, the more difficult and costly the cleaning and drying process.

For the accommodation of both the male and female anatomies, and aesthetic preferences as well, I have discovered that tailored garments hold great promise due to the increase of material choices and tailoring methods. Because the male and female are anatomically different, tailoring of diapers, briefs and the like accordingly should reflect their individually.

The umbilicus of newborn babies is a very tender area for about ten days following birth. Efforts have been extended to protect this area while the umbilicus is healing. However, no diaper of which I am aware adapts to the anatomy of this unhealed navel cord while snugly fitting the rest of the infant's abdomen, avoiding leakage, while preventing avoidable rubbing and irritation.

Finally, fasteners of diapers seen in the prior art tend to wear and crinkle and their edges are sometimes sharp enough to injure a person. I am not aware of a fastening tab whereby, the tabs themselves have been constructed to have softened edges while increasing adjustability and function of tab.

DISCLOSURE OF THE INVENTION

Accordingly, one advantage of the invention is in producing improved leakproof undergarments for infants and adults of both sexes.

Another advantage of the invention is in producing improved leakproof undergarments that are tailored to the anatomy of the wearer.

A further advantage is in producing leakproof undergarments that incorporate disposable or reusable fluid absorbent pads that are snugly fitted to the pubis area of a wearer without use of adhesives.

Another advantage is in producing leakproof urinals that can be used independently of, or attached and worn in, existing undergarments.

A further advantage of the invention is in producing a filamentary fastener of improved construction having particular utility for securing a tailored diaper to the body of a wearer.

Another advantage is in producing a fastener of the above type having a property of enhanced adjustability.

A further advantage of this invention is to disclose a new fastening tab, whereby the edges of the nylon hook and loop fastening tabs are sealed in soft threads and protect sharp edges from hurting anyone. It will be a further object of the invention to claim a manufacturing procedure to not only efficiently assemble the tab for durable use but to also disclose a quick low cost way to do so.

A further object of the invention is to provide a lower cost, leak-proof garment, a diaper cover which retains a pad in a secure way by a simple folding of fabric . . . folded fabric forms a frontal pocket tailored to secure the whole pad while avoiding difficulty in cleaning in the rear portion.

Another advantage is in producing fluid absorbent reusable pads for diapers and the like, having superior fluid absorbing construction and improved rapid drying characteristics for cleaning.

A still further advantage of the invention is in reducing damage to the ecology by minimizing unnecessary disposal of undergarment pads, etc., while encouraging washing only of necessary undergarment parts.

A still further advantage of the invention is in improved techniques for manufacturing leakproof undergarments and urinals.

The above and other advantages of the invention are provided at least in part by a waterproof diaper shell having inner and outer surfaces, and an elongated sling of material having its upper and lower ends attached through a pair of connecting pieces to, and its opposite sides free and floating on, the inner surface of the shell. The opposite sides of the sling fit in the crevices on opposite sides of the pubis of a wearer, the sling having a main surface facing away from the shell and establishing a channel to entrap and isolate fluid within the sling. A line of attachment between at least one end of the sling and its connecting piece is arcuate to recess the channel within the opposite sides and conform the channel to fit the pubis of the user when the diaper is worn.

Preferably, the lines of attachment between both ends of the sling and the pair of connecting pieces are arcuate. Opposite sides of the sling are covered with an elastic trim, and pull on the connecting pieces by the trim helps to shape the ends of the channel into a curve to conform to the arcuate lines of attachment of the sling to the connecting pieces. The trim, connecting pieces and arcuate lines of attachment together recess the sling to pocket and tailor fit the sling to the pubis of the wearer.

Opposite sides of the shell form legholes, and at least a portion of the periphery of the shell at the legholes is covered with a second elastic trim to fit the legs of the wearer.

In accordance with a particular embodiment of the invention, the sling comprises a common piece of waterproof material integrally forming an underlayer and the opposite sides of the sling. The waterproof underlayer and waterproof opposite sides are demarked by a fold line sealed and covered by elastic trim. The sling preferably comprises a first piece of waterproof material forming a waterproof sling underlayer and second pieces of waterproof material forming the waterproof opposite sides of the sling. The waterproof underlayer and waterproof opposite sides of the sling are sealed together and covered by elastic trim.

Other embodiments include an additional layer of material overlying an outer surface of the diaper waterproof shell, or a transverse band of material overlying and attached to one end of the diaper shell at the sling to establish a waist band. This waist band preferably is attached to the sling along an arcuate line of attachment.

Furthermore, the embodiments also preferably include a fluid absorbent pad insert positioned in and laterally retained by the recessed arcuate ends of the channel. The pad insert advantageously will of a type that contains a fluid absorbing chemical gel material.

In accordance with another aspect of this invention, a device for use in securing a garment to the body of a wearer comprises at least one strip of filamentary fastener material on an outer surface of the garment, and strips of complementary filamentary fastener material extending elsewhere from the garment for attachment to the strip when the garment is worn. The complementary filamentary faster material strips comprise a first strip of loop-type filamentary material having one portion attached to the garment and the remaining portion extending therefrom, the strip oriented with its loop bearing surface in the same direction as the outer surface of the garment. A second strip of loop-type filamentary material attached to a portion of the first strip overlies the shell and is oriented with its loop bearing surface in the same direction as the inner surface of said garment, A third strip of hook-type filamentary material is attached to the same side of the first strip as the second strip. In the preferred embodiment, the second and third strips are spaced apart from each other on the first strip, and the region of the first strip residing between the second and third strips establishes a hinge. The third strip of hook-type filamentary is spaced apart from the terminal end of the first strip for comfort to the wearer.

The first strip of loop-type filamentary material may be die-cut. The third strip of hook-type filamentary material preferably is rectangular, and one end of the rectangle is spaced apart from the terminal end of the first strip.

In accordance with still another aspect of the invention, a fluid absorbent pad insert for use in a diaper comprises multiple layers of fluid absorbent material projecting from a common seal and having ends freely floating. The layers of fluid absorbent material each present opposite fluid evaporation surfaces exposed to air.

Preferably, the layers are elongated in shape, and the common seal extends longitudinally or laterally. The common seal may be located at one end of the multiple layers, or may be staggered relative to each other along the common seal. The layers furthermore may be approximately V-shaped and have a base facing a common direction.

In accordance with another aspect of the invention, a tailored urinal comprises a diaper shell of waterproof material, and the shell has an inner liner of fluid absorbent material circumscribed by waterproof material. The peripheral edge of the shell is covered by an elastic trim, and one end of the shell is arcuate in shape, bifolded and jointed to form a cusp.

Preferably, one end of said shell carries a waist strap to wrap around the wearer. The opposite end of the shell has an extended layer of waterproof material folded inwardly to form a cuff. The inner surface of the shell has an elastic strap to retain a pad insert.

In accordance with still another aspect of the invention, a tailored urinal adapted to fit within underwear comprises an elongated, approximately rectangular diaper sling of waterproof material having opposite sides defining crevices on opposite sides of the pubis of a wearer. The sling has an inner liner of fluid absorbent material including opposite sides of waterproof material to isolate the pubis from escape of fluid from the sling. The inner liner is of length less than that of the sling and has a frontal end floating to receive and pocket a fluid absorbent pad insert. A fastener may be located at one end of the sling for retaining the urinal about the waist of a wearer.

In accordance with another aspect of this invention, a tailored urinal adapted to fit within underwear comprises an elongated, approximately rectangular diaper sling of waterproof material having opposite sides defining the sides of the pubis area of a wearer. Within the sling, an inner liner of fluid absorbent material has opposite sides of waterproof material to isolate the pubis area from escape of fluid from the sling. The inner liner is of a length less than that of the sling and has ends of waterproof material infolded to receive and pocket the ends of a fluid absorbent pad insert. At least a portion of the peripheral edge of the sling is covered by an elastic trim. A fastener is implemented for retaining the urinal inside an undergarment.

As an additional aspect of the invention, a slip-on underwear comprises an underwear garment formed of an hourglass piece of material folded and joined on opposite sides by garment waist-to-leghole seals. Within the underwear garment, an elongated sling of material has its upper and lower ends attached through a pair of connecting pieces to, and its opposite sides free and floating on, the inner surface of the garment. The sling has a main surface establishing a channel to entrap and isolate fluid within the sling. A line of attachment between at least one end of the sling and its connecting piece is arcuate to recess and conform the channel to fit the pubis of the user when the sling is worn. Opposite sides of the connecting piece at at least one end of the sling is sealed within the garment leg-to-waisthole seals.

In accordance with another aspect of the invention, a urinal to be worn by a male comprises a generally tubular receptacle of waterproof material having an upper end adapted for attachment within an inner surface of a garment and positioned for receiving the penis of a wearer. The wall of the tubular receptacle facing the penis is opened longitudinally to define flexible "wings" surrounding a penis entry opening. Fasteners formed on the wings retain the entry opening about the penis.

Preferably, the fasteners comprise filamentary fastener strips, positioned on the receptacle to enable the strips to adjustably define the diameter of the penis entry opening.

In accordance with a preferred embodiment of this aspect of the invention, an undergarment retains the receptacle. A pocket is formed on the inner surface of the undergarment, beneath the pubis of a wearer, to retain the receptacle.

Optionally, there may be provided a fluid absorbent pad insert within the receptacle. Inner edges of the wings are arc-shaped to accommodate varying anatomy of the penis. In one embodiment, one of the wings is fixed and the other swings free.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF DRAWINGS

FIG. 1 is a perspective view of a reusable diaper having a waterproof diaper shell and floating sling, in accordance with one aspect of the invention.

FIG. 1(A) is a top view showing the inner surface of the diaper with sling, fluid isolation barriers and absorbent pad.

FIG. 1(B) is a detailed view showing the construction of a filamentary fastener strip depicted in the previous figures.

FIG. 3 is a perspective view of another embodiment, with "butterfly" fluid absorbent pad and filamentary fastener strip and cover assemblies of novel construction.

FIGS. 3(A) and 3(B) show construction methods for the filamentary fastener strips and covers implemented in the invention.

FIG. 12 depicts a new manufacturing procedure for constructing tabs with an over-look stitch, loop and hoop material back to back sealed on edge with stitch of overlock machine.

FIG. 12(A) The continued process of forming fastening tab by a second row of overlock switches.

FIG. 12(B) A third view of process of forming tab by showing stitches sealing end of tab in a continuous cut out stitch process.

FIG. 12(C) The finished tab with the exterior edges of two pieces of material sealed.

FIG. 13(A) is a top view showing an inner surface of the formed sling with its frontal pad pocket formed of the sides turned in.

BEST MODE FOR CARRYING OUT THE INVENTION

Figure 2:
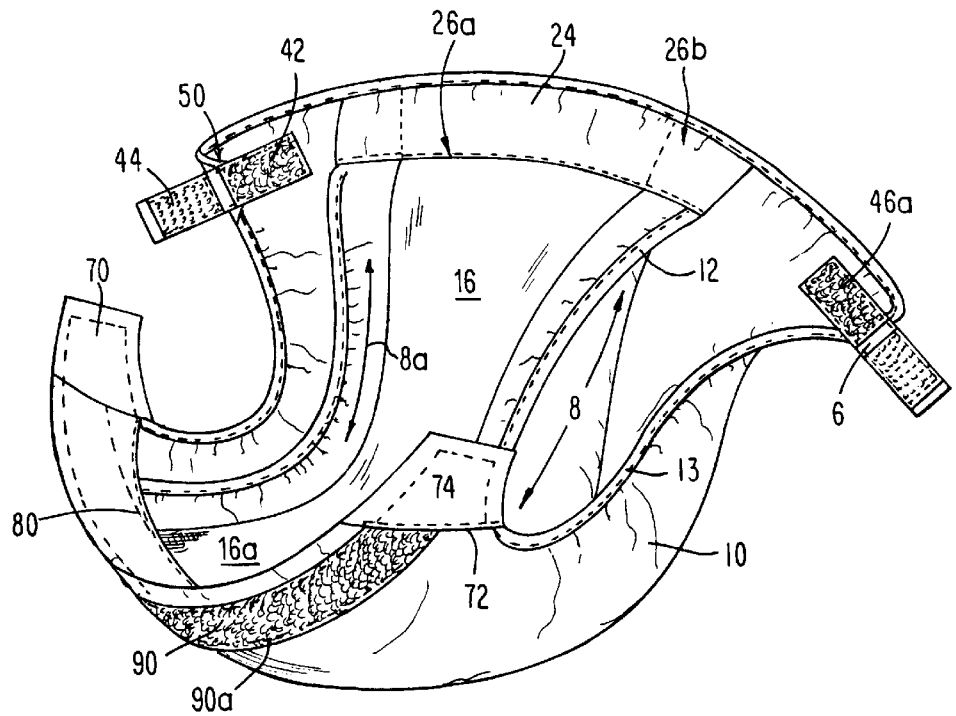
FIG. 2 is a perspective view of another reusable diaper embodiment.

In FIGS. 1 and 1(A), a tailored diaper 10, in accordance with the invention, comprises an outer, waterproof shell 10, which may be hourglass-shaped as shown or other suitable shape. A strip of waterproof material 8, termed a "sling," has its upper and lower ends floating between the legholes of the shell. A connecting piece of material 24 of the sling 8 is joined to the shell at elastic trim 13. The opposite end of the sling is attached at trim 13 through a waterproof strip 32 of width equivalent to the width of the shell 10A and residing circumferentially at the trim 13. This strip is termed a "arc frontal bumper" herein. A connecting piece of waterproof fabric is curved at a frontal end as shown and this elasticized curve creates a pouch in the bumper.

Within the waterproof sling is an absorbent core 16A that is of a width less than that of the sling. The length of the pad is less than that of the diaper shell. Hence, the sling 8, sized as described, together with connecting waterproof strips 24 and 14 at the ends of the pad, join with fluid isolation strips 8A surrounding the fluid absorbent core 16A to form cradle channel 16.

The lines of demarkation separating core 16A and bumpers 14 and 24, respectively, are arcuate, as best shown at 80 in FIG. 1(A). This arcuate joining establishes a cupping action to the core 16A and strips 8A, causing the surface of the core 16A to become recessed beneath the strips 8A and bumpers 24 and 14 to encase the pubis of the wearer. Hence, the strips 8A are termed "drop strips" hereinafter. This cupping action is enhanced by elastic trim 12 on the edge of the sling 8 so that the entire cradle will cup the pubis tightly and retain fluid thereat.

As mentioned previously, circumscribing the entire diaper shell 10 is the second elastic trim 13 that causes the shell to embrace the pelvis, stomach, buttocks and legs while holding sling tight against just the central pubis, and tailored according to the invention to do so. Hence, the body fluids discharged from the wearer will become absorbed directly into the core area 16A of the sling, with the drop strips 8A and strips 24 and 14 restricting the fluid from escaping the channel 16. Any fluid that overflows the drop strips 8A will become contained within the waterproof shell 10A and will become dispersed along the inner surface of the shell, tending not to leak out through the legholes or any area where second elastic trim 13 conforms the outer shell to the body torso.

The diaper is secured to the body of the wearer by hook-type filamentary fastener strips 44 that project outward from the corners of the rear portion of the shell 10A. These hook type filamentary fasteners 44 are positioned to wrap around the waist of the wearer and couple to loop-type filamentary fastener strips 30 at the front portion of the outer surface of the shell 10A.

The loop-type filamentary strips 30 are arranged in a V-pattern on the front surface of the shell. This pattern, together with the arcuate construction of 32, tends to produce a pouch just above the V-pattern so as to protect the umbilicus of an infant wearer. The force of the hook-type fasteners 44 pulling on the V-shaped filamentary strips 30, together with elasticized curve of the connecting piece 32, form a novel projecting material just under the infant's navel. The pouching effect further reduces irritation to the umbilicum.

Referring to FIG. 1(B), the fastener strip 46 comprises a first length 40 of loop-type filamentary material sealed over the full length of tab 46 or just the end portion of 46A. Loop tab 46 faces away from loop tab 40 as 40 seals over the end of 46A. The soft loop portion of tab 40 faces the inside of diaper shell 10. The soft loop portion of tab 46 faces outside the diaper 10. This underside surface of the loop material 46 becomes the receiving device for a rectangular piece of hook type filamentary material 44, sealed centrally with opposite ends 4 sealed under 40 at joining point 6 or 40A.

The region 4 of strip 46 is devoid of hook-type filamentary material and forms a hinge to enable the hook portion 44 to fold into contact with the loop portion 40, enabling the loop portion 40 to cover and protect the hook portion during washing. The region 4 tends to develop a "memory" which, together with the weight of hook-type filamentary region 44, causes the strip to fold during washing so that the hook 44 and loop 40 filamentary materials will mate, and the hook-type material swings on its weighted hinge 4 to cover the hook material during washing. The terminal end portion of the strip at 46b is also devoid of hook-type filamentary material to avoid discomfort to the wearer as the end of the strip presses against the thumb when opening the tab and can hurt the skin of the thumb.

Figure 2A:
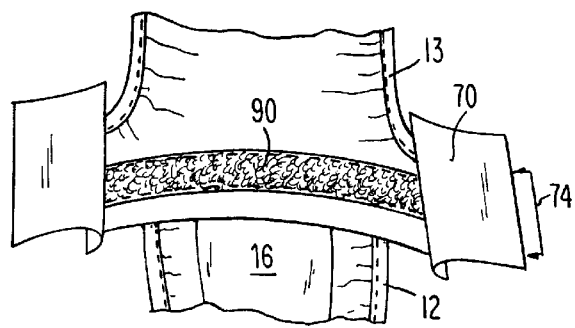
FIG. 2(A) is a detail showing attachment of the fastener strips to the diaper shell of FIG. 2.
Figure 2B:
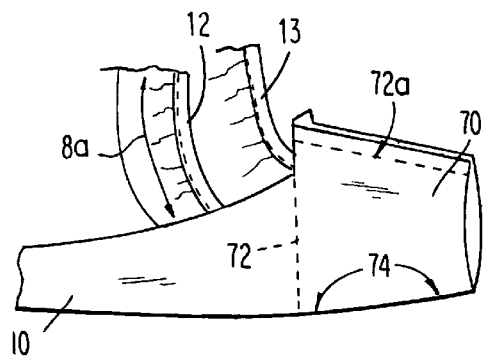
FIG. 2(B) is a detail showing a protective wing construction incorporated in the embodiment of FIG. 2.
Figure 2C:
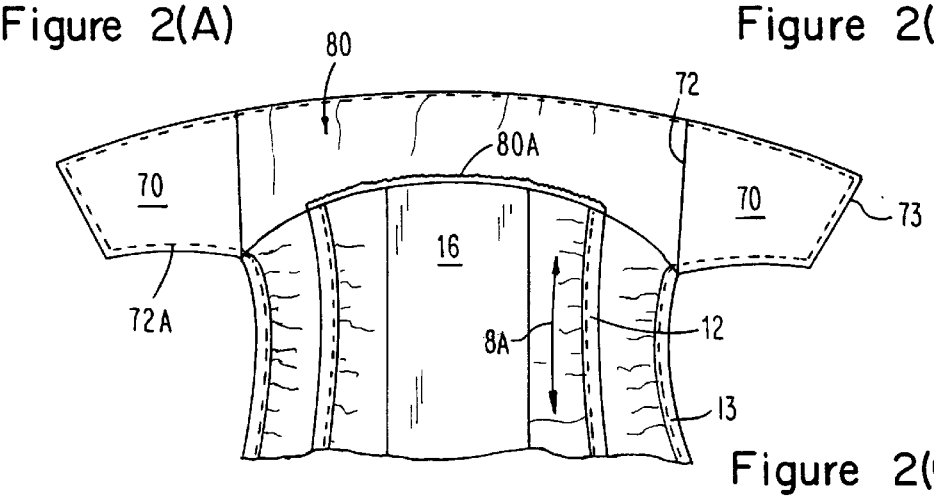
FIG. 2(C) is a more complete view of the protective wing construction of the preceding figure.

Referring to FIG. 2, a second embodiment of a diaper, constructed in accordance with the invention, is similar to that of FIG. 1. However, loop-type fastener 90, on the stomach portion of the diaper, has its ends attached beneath protective wings 70, whereas the counterpart strip 30 of FIG. 1 is characterized by open sealing. In FIG. 2(A), fastening bar 90 has its end portions inserted in protective wing 70 as protective wing 70 overlies the strip 90 and is fastened both to the shell and strip by a joining line 72. The assembly is made by first joining bar 90 along the edges 90a and 90b before folding bumper 80 inward or attaching wing 70. Then wing 70 is attached at joining line 72 sealing the ends of bar 90 as shown in FIG. 2A. Fold line 74 turns channel 16 to the outer back side of diaper 10 so as to join the wing sides to each other on line 72a. Next, channel 16 is flipped to inside of garment. Wings 70 are turned inside out leaving only the most exterior end 73 open for sealing of the finished garment. Ends 73 may be finished off either by folding them inward and top stitching, such as lines 72a of FIG. 2(C) illustrates, or they could be finished in some other sewing or sealing method.

Another novel feature of FIG. 2 is in the rear bumper strip 24 between the pad surface 16a and the diaper shell elastic 13. This bumper strip 24 is joined to the shell along arcuate line 80 to produce the cupping and recessing of the channel 16 as explained previously. In addition, the ends of the strip 24 are folded back and joined at 26b to present additional strength to the assembly, avoiding tearing during multiple use and washing. Line 26b is partially formed as arcuate sealing line 80 seals the folded pieces of material.

As in the embodiment of FIG. 1, the cradle of the FIG. 2 embodiment is cupped by the action of arcuate sealing of 26b in 80 together with drop strips 8a.

Referring now to FIG. 3, another embodiment, similar to FIGS. 1 and 2, illustrates how the recessed channel 16 accommodates an additional absorbing pad insert 19, which does not move about because of recessed structures bordering the pad insert on four sides; 8A (drop strips), 24 (arc rear bumper) and 71 (arc belly band), which works to recess the frontal end of the diaper in same fashion as arc frontal bumper 14 of FIG. 1 and folded end of diaper shall 10A of FIG. 2. Like FIGS. 1 and 2, the cradle channel conveniently receives pad insert 19 and stabilizes this absorbent pad. The pad fits the cradle because of the cupping action. Additionally, fabric-to-fabric contact between the external pad 17 and internal pad surface 16A presents substantial surface friction and minimizes shifting of the pad insert.

FIG. 3 also illustrates a decorative fabric outer layer 11 over the surface of diaper shell 10. In addition, a stomach band 71, overlying and attached to the stomach portion of the diaper 10a carries a loop-type filamentary fastener strip 90. The band 71 encases the diaper shell, sling and pad by join lines 71a and 71b. Line 71 does not penetrate the underlying waterproof fabric at join line 92 or sealing line 90a. Hence, the fastener strip 90 is attached to band 71 without penetrating the underlying waterproof fabric.

Tabs 48, extending from the rear corners of the inner surface of the diaper shell 10A, may be formed and secured to the diaper by a continuous line of stitching or other sealing process. Each strip comprises a single strip of loop-type filamentary material which is inverted (folded inward), shown in FIG. 3(A), and folded back on its loop-free side to establish a face presentation of loop filamentary material 47. At the other end is positioned a rectangular strip of hook-type filamentary material 44, attached to the loop-free back side of strip 47, leaving space 44 (without hook material) defining a hinge. The opposite end, also hook-free, establishes the pull tab 46A, as explained previously. The loop-type strip 47 is now bar-tacked to itself at 6.

Figure 4:
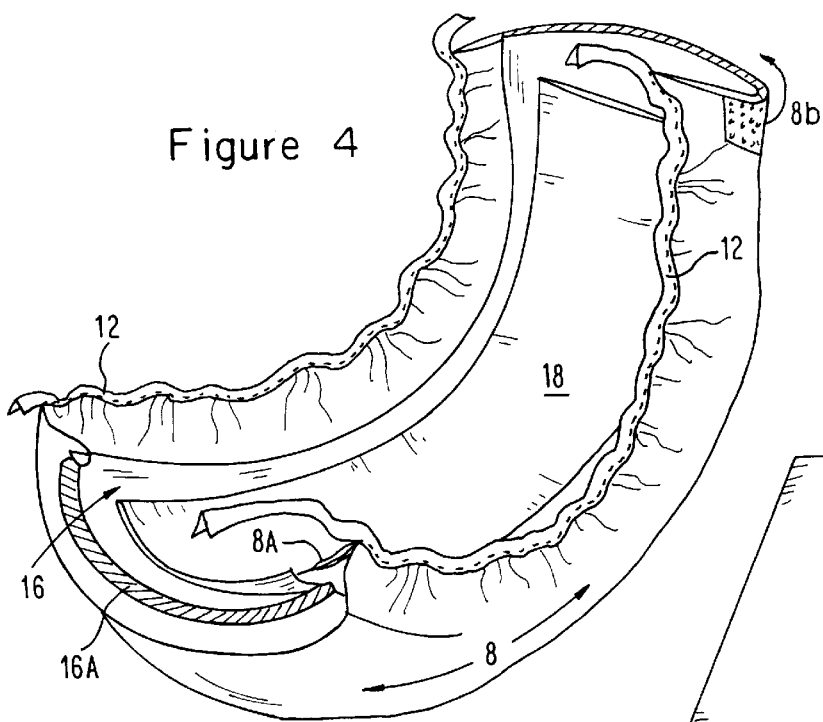
FIG. 4 is a perspective view of a novel fluid absorbent diaper, adapted to be worn within underwear.
Figure 4A:
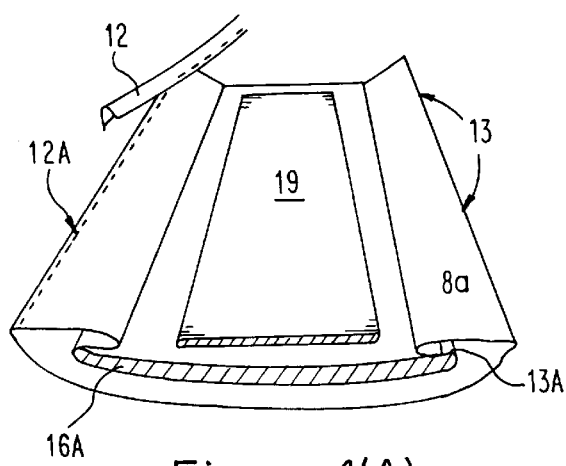
FIGS. 4(A) and 4(B) show construction details associated with the embodiment of FIG. 4.
Figure 5A:
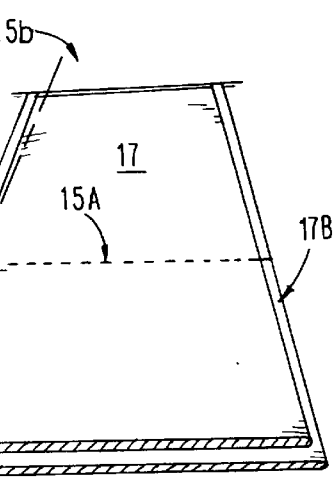
Figure 4B:
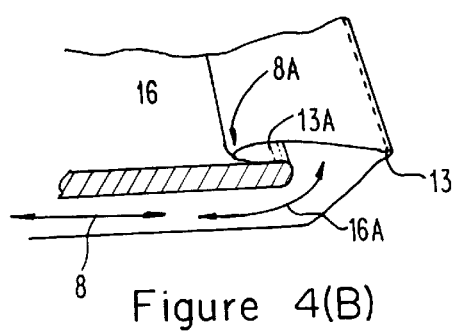

Referring now to FIG. 4, a detail of the channel construction (shown separated from the diaper shell for simplicity) is depicted. The internal construction of the channel is illustrated in FIG. 4(A), with drop strips 8a joined to channel sling 8 beneath elastic trim 13, and also joined to the periphery of core pad 16a. Hence, the core is suspended by the drop strips enabling the channel to shift laterally to accommodate the pubis while cupping to contain and restrict flow of fluid. Drop strips 8A are formed when fold line 13 is inserted in elastic trim 12. To define the fold line 13, sealing of 12A is an option before adding the elastic trim. A fastening means 8b, such as a filamentary fastener strip, is provided if the channel is detachable from the shell 10A at arc bumper 24.

Figure 5:
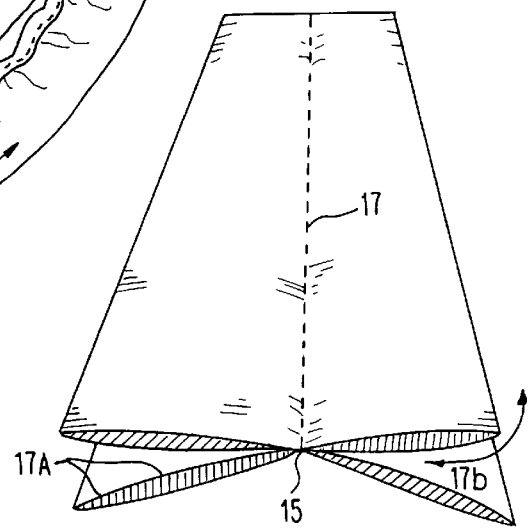
FIGS. 5 and 5(A) are views of two different "butterfly" pad constructions in accordance with the invention.

Referring to FIG. 5, depicted is an absorbent pad 17, adapted to be seated in the cradle 16 shown in the preceding figures, of a novel, multiply layered construction. This "butterfly" construction is formed of two elongated pad layers, bisected longitudinally by a joining line 15, to establish a pad of eight effective evaporation surfaces, each spanning the length of the pad and one-half its width. The resulting pad is thin but will tend to dry much more quickly than a single pad layer as its multiple evaporation surfaces are exposed to air.

The same principle can be applied by forming the multiple layered pad with a transverse stitch line 15a, and preferably the outer layer is slightly larger than the inner layer.

Figure 6:
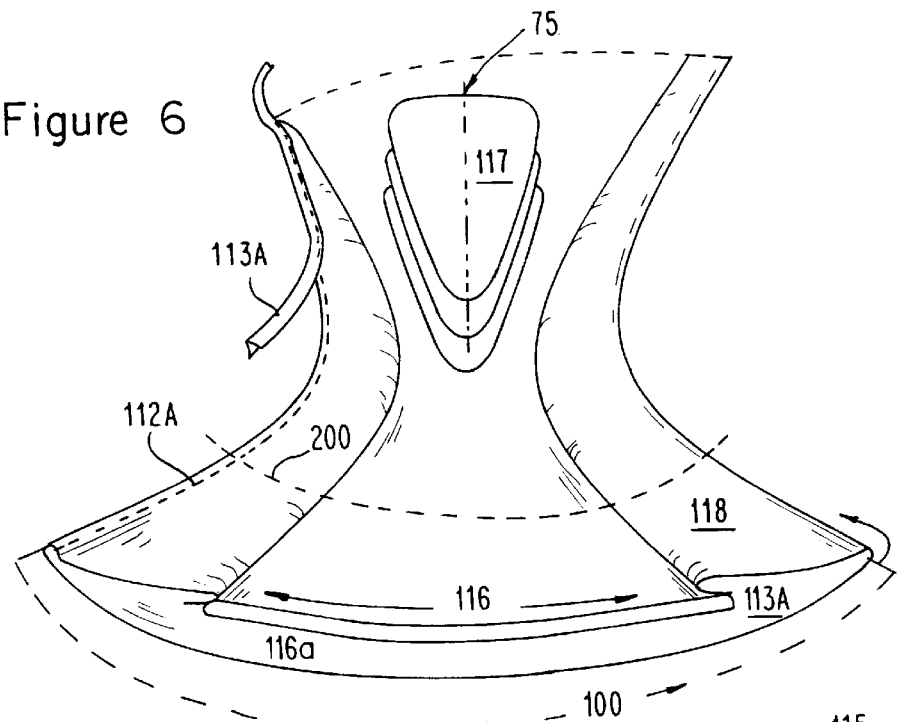
FIG. 6 is a view of a fabric urinal, per an aspect of the invention, in an intermediate state of construction.
Figure 6A:
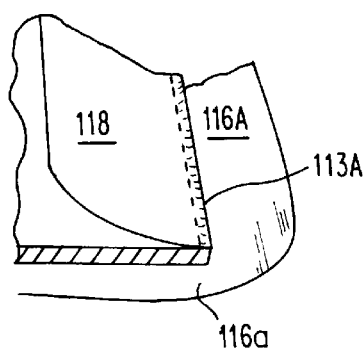
FIG. 6(A) is a detail showing how the fabric urinal is fabricated.

As another alternative, the layers may be stitched together at one end or side to present additional evaporation surfaces (not shown). 15b shows the possibility of an arc cut end to the pad for insertion in arc bumper 24 of FIG. 6 or to be used separately.

Referring now to FIG. 6, a novel channel structure of this invention is implemented in an adult garment or extra large child size. The configuration of the shell embodying the channel is of hourglass-shape, with dropstrips 118 separate, rather than folded, beneath elastic trim 112a. As seen in FIG. 6, the process of applying elastic 112A to the edges actually pulls the end of channel into a natural arc 122 for fitting to an arc bumper to be attached to an adult size shell (not shown).

Figure 7:
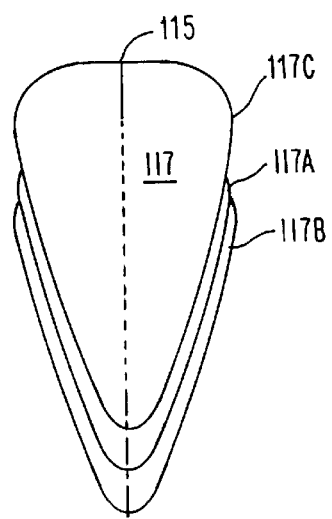
FIG. 7 is a view of a novel absorbent pad of staggered V-shaped layers utilized in the urinal in FIG. 6.
Figure 7A:
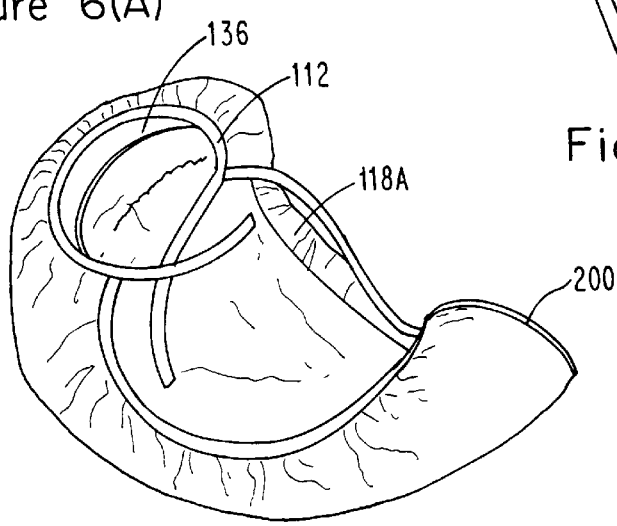
FIG. 7(A) shows the urinal of FIG. 6 in a final stage of construction.

Internal core 116 is also of hourglass configuration to conform to the shell. The internal construction of the channel at 116A is the same as in FIG. 4(A) of the previously disclosed embodiment, except waterproof material undersurface 116A may be extended to line 100 and folded inward to form a cuff 136 as shown in FIG. 7A. The core 116 accordingly is able to shift laterally while remaining relatively fixed in the longitudinal direction and suspended by drop strips. A V-shaped pad insert 117, having the "butterfly" multiple layered construction, is positioned on the channel beneath elastic strips 119. The V-shaped pad insert 117, shown in more detail in FIG. 7, comprises multiple layers 117A–C, aligned laterally and staggered longitudinally.

Another aspect of the invention, shown in FIG. 7(A), a fabric urinal for bedridden patients is formed by cutting along the arcuate line 200 in FIG. 6, and sealing the now exposed edge together to establish the receptacle shown in FIG. 7(A). The joined end 200a is positioned between the legs of the wearer, and optional straps 112 wrap around the waist for stability. Within the urinal shown is located the absorbent pad insert 117 of FIG. 7, conveniently removed and laundered for reuse. Alternatively, the pad 117 of FIG. 7 could be replaced by a disposable gel-filled pad of similar V- or teardrop shape. The urinal can be folded flat, slipped under the patient and opened to cup the pubis, a novel process considerably more convenient, efficient and comfortable than conventional hospital bed pans.

Figure 8:
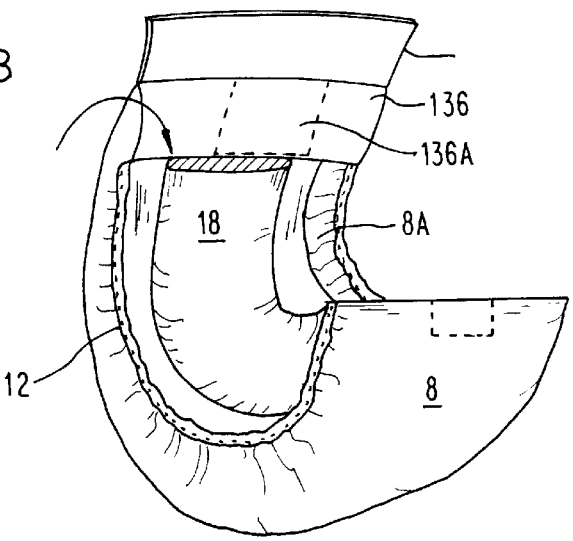
FIG. 8 is a perspective view of a urinal of cuffed construction, adapted to be worn within underwear, in accordance with another aspect of the invention.

Referring to FIG. 8, the embodiment shown is a detachable urinal construction, the details of which have been described in connection with FIG. 4. In FIG. 8, disclosed is a method of closing the ends of the channel by a fastening means 150, which adapt for attachment to garment shell 134, on the central outer portion of the underside of cuff 136b. The corresponding attachment means 150a, on underside of cuff, could be a hook filamentary fastener for the underside placement would protect it from destruction in the wash. The urinal could then be closed at 150 with loop-type filamentary fastener material, which needs no cover in the wash. The closings of the ends of sling 8 form pockets for receiving an additional fluid absorbent pad insert 19 as shown. There will be no slippage as a result of fabric-to-fabric contact in addition to the closed ends of the urinal.

Figure 8A:
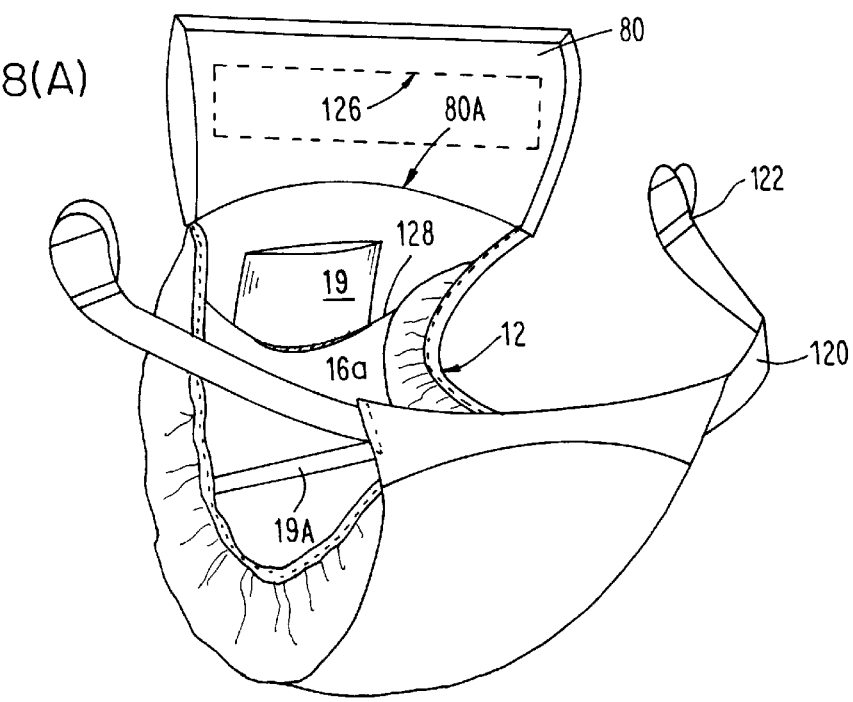
FIG. 8(A) is a perspective view of a modification of the embodiment of FIG. 8, having waist belt pad pocket.

In FIG. 8(A), the outer waterproof garment shell 134 is shown with a belt 125 formed preferably of an elastic material having loop filamentary fastener strips 120 and 126 sealed at 122 to be mated for closure and opening at pull tab 124 to wrap around the waist of the wearer and couple to a complementary filamentary strip 136a on the stomach portion of the shell. Elastic strips 125 receive reinforcement sealing under the folded backband at the rear end of garment 134 at sealing lines 135.

Figure 8B:
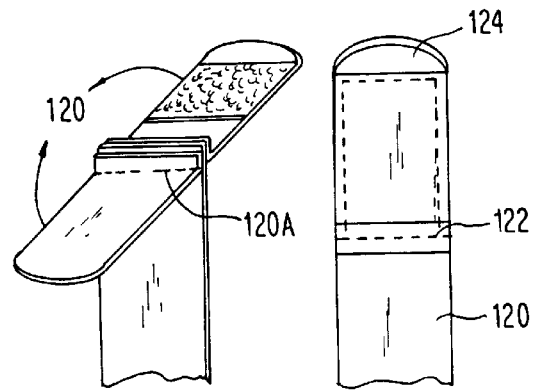
FIG. 8(B) shows construction details of filamentary fastener strips, incorporated in the invention.

The fastener strips at the end of the belt 125 may be of the novel construction shown in FIG. 8(B), with strips of hook and loop type filamentary material applied on opposite sides of the belt 125 and wedging the raw end of the belt between the complementary fasteners. All three raw ends, the raw end of loop 120, the raw end of belt 125, and the raw loop end of 120a, are stitched at line 122. Hook 126 is positioned centrally and fastened to tab 120a (the back side of tab 120a), which will also become the inside of the tab when closed. Hook material 126, now fastened securely to 120a by either sealing or sewing, is ready for closure and hiding of the raw ends; however an additional joining or stitch line 122a will be necessary to encase the raw ends permanently.

Figure 9:
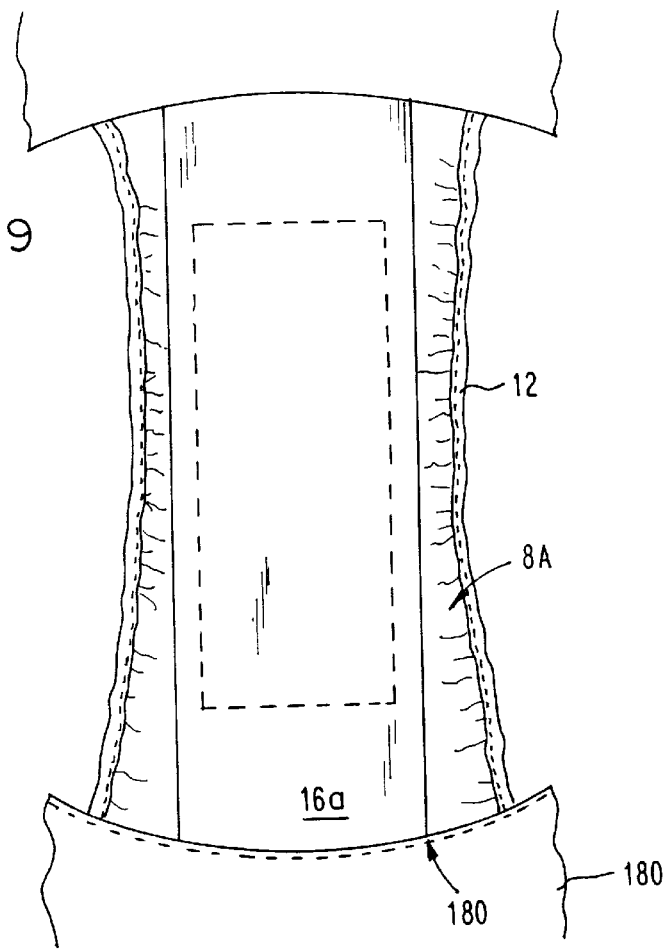
FIG. 9 depicts a diaper retaining an absorbent pad and adapted to be worn within, but separate from, underwear.

FIG. 9 depicts what is referred to herein as a double sling, with both waterproof materials 8 and 8b encased in elastic trim 12 just as other embodiments of same rectangular shaped urinal. However, core 16a is not sealed at arcuate line 80; instead it is left open at pocket 128 for receiving a pad insert 19. The purpose of the double sling is to allow tailoring of inside sling without leakage, if sewn. Hence pocket 118 may be sealed at the end and yet waterproof fabric 8 covers it. The same is true for the opposite end, that is, arcuate line 80, if sewn, will not leak because of the unpierced fabric outer shell 8 just behind it. FIG. 8(A) has same suggested fastening means as FIG. 8.

Figure 9A:
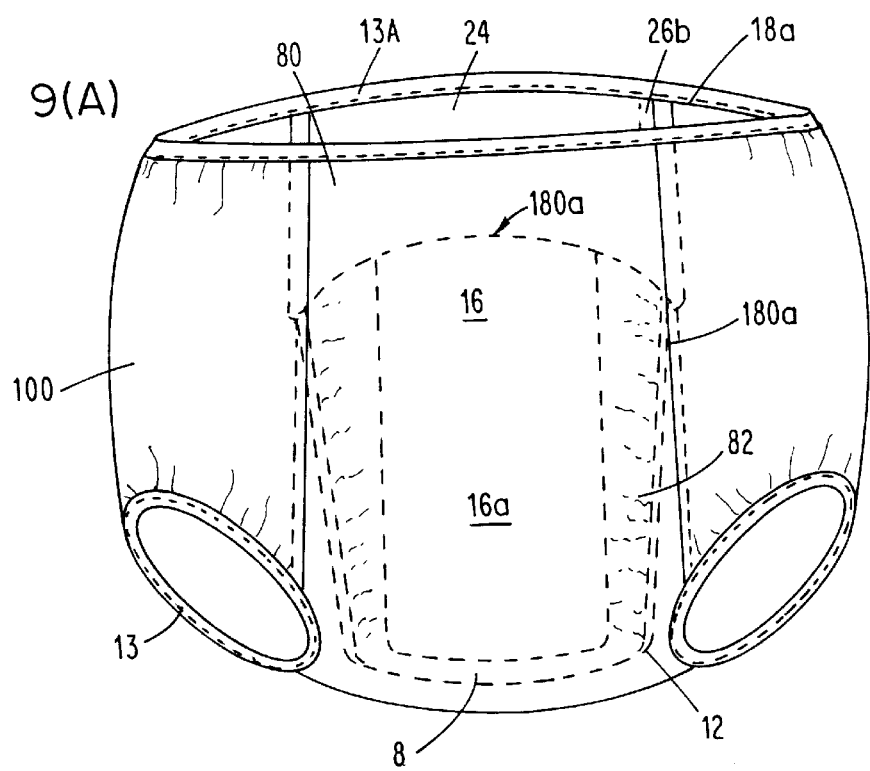
FIG. 9(A) view of two different underwear containing an integral sling for separating fluid from the legholes.

Referring now to FIGS. 9 and 9(A), the rectangular urinal of FIG. 4 and the hourglass urinal of FIG. 6 are adapted to be inserted inside a pull-up pantie or side-fastened pantie which may be pulled down or unfastened to be removed. In FIG. 9(A), fabric pantie 180 with the "right" side of the fabric outward, a side fastening means is adapted with snaps, at waist and leg hole and corresponding filamentary fastener strips in-between. The combination of filamentary fastener strips, supplemented by snaps (snap-tape, etc.) for strength, is novel for such panties. Other fastening means such as zippers, snaps etc. could be substituted or the fastening on side may be removed in favor of a sealed or sewn joining line 13a as shown in FIG. 9(A). It is also possible to fasten only one side of the garment, such as seen in skirts etc. for easy removal.

The arc-bumper shown in FIG. 9 is called herein an arc-liner, 80b, and the arc insertion line 80A suspends the urinal so that leg holes 13 are completely free for fitting the legs of the wearer. The channel of FIGS. 4 and 6 (depending on whether a toddler or adult, respectively, is being accommodated) is suspended by arc-liner 80b forming cradles for pad insert 16a to fit snugly against the pubis.

All the same principles of design in this disclosure that are novel are applied to the pull-up pantie as seen in the case with all previously disclosed embodiments. Choices of fabrics are available that are waterproof for the panties, but also of stretch quality like a water-resistant lycra or Gortex™, etc. type material. The stretch quality of fabric is not essential, but recommended for snug overall fit of channel against the body. It should be remembered that hook and loop fastening of previous embodiments would give a circumferential fit, and pull ups rely on stretch fabric to accomplish that goal with more satisfaction to the wearer. There is also the possibility of garment appearing less bulky if the pull ups is of outer water-resistant material of stretch quality.

The embodiment of FIG. 9B is constructed like sling 8 seen in FIGS. 1, 2, 3, 4, 8, 9, and 9A, but it is not attached to the arc bumpers (liners). Sling material 8 is extended to the waist elastic trim. Pad insert 16a absorbs sufficiently for light incontinence needs, recessed by waterproof sides 8a and encased by elastic 12. Sides of stretch material join at four seams 3b. The fit of the pantie at the waist and leg holes is adjusted by adjustment strips 212, 218 shown as snap tape but implemented in other forms, such as filamentary fastener strips.

Figure 10:
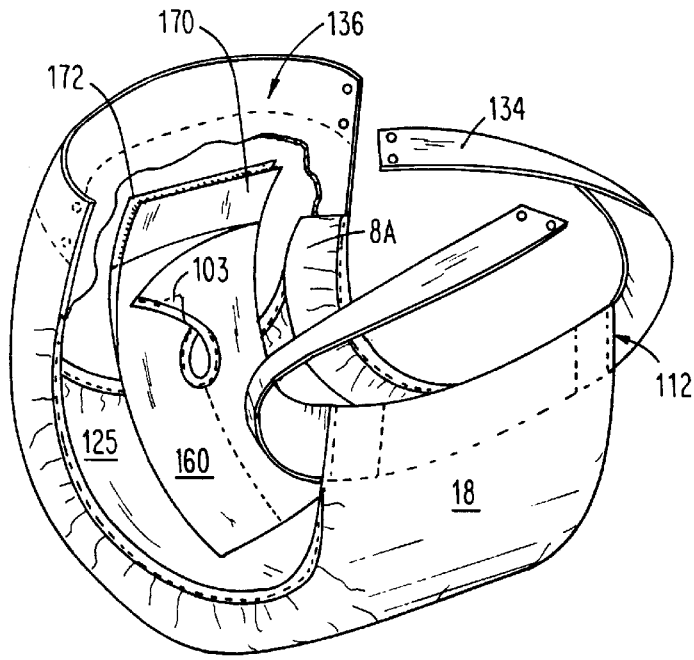
FIG. 10 is a perspective view of a fabric urinal designed to be worn by men.

Referring now to FIG. 10, the basic channel structure of this invention can be used to accommodate a urinal for males. The urinal comprises a waterproof shell 18, pocketed at 125, and establishing a channel as in the previously described embodiments. At one end of the channel is a cuff 172 for retaining, with filamentary fasteners or other suitable fastening means, one end of a novel male bag or receptacle 160, tubular in shape to receive the penis. The receptacle 160 has its lower end folded at 106 as shown in FIG. 11(B).

Figures 11, 11A, 11B:
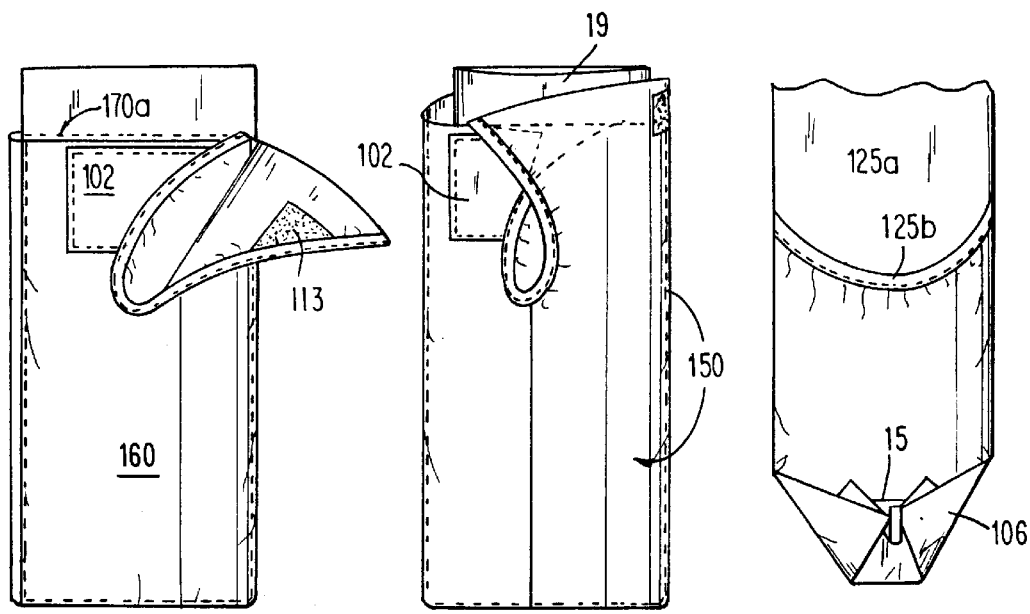
FIG. 11 is a detail showing the construction of the fluid retaining receptacle of FIG. 10.
FIG. 11(A) shows the "arc-wing" construction of the receptacle for adjusting the size of the penis entry opening.
FIG. 11(B) shows the construction of the receptacle pocket retained within the shell of FIG. 10.

At the upper end of the receptacle, the receptacle wall is separated longitudinally and trimmed with elastic, as shown in FIG. 11(A), with its upper ends of an arcuate configuration, adapted to swing together and close around the stem of the penis. The outer wing of this structure is fitted internally by a strip of filamentary fastener material 113 positioned to attach to complementary filamentary material 102 on the underlying portion of the receptacle. By adjusting the position at which the two strips of the filamentary material attach, the receptacle can adapt to males of varying size.

Preferably, the receptacle will receive a pad insert of fluid absorbent material, preferably of the gel-filled variety, which can be removed following use and replaced.

As an alternative, the receptacle 160 can be non-releasibly secured to the shell 8, or even removable and disposable.

Formed within the inner surface of the shell is another pocket 125, having an elastic opening, to receive and position the receptacle 160 after the penis is inserted.

The folding of the receptacle 160 at 106 as shown in FIG. 11(B) eliminates the need for seam sealing the bag to prevent leakage. Any leakage, however, will be retained by the pocket 125 within the shell 10.

FIG. 12 discloses a manufacturing procedure whereby a new tab for fastening diapers is formed with soft, sealed edges 206A, B, to protect the wearer when in use. The procedure involves four steps. First, as shown in FIG. 12, the Hook pieces 200 are placed on the back side of a continuing loop strip 202, spaced apart as shown and connected in a continuous overlock stitch line 206B which seals one edge. FIG. 12A, the second step, seals the opposite edge 206A with a continuous stitch line of same overlock methodology. Now that the opposite edges are sealed, step three seen in FIG. 12B is fed into an overlock machine that cuts the tab at 210 and then connects it to a continuous line of overlock stitching 208. FIG. 12C is the finished tab-fastening structure to be used on any of the diaper prototypes, with three edges sealed for protection of the wearer from sharp edges and the extending loop strip 202 establishing a hinge.

Figure 13:
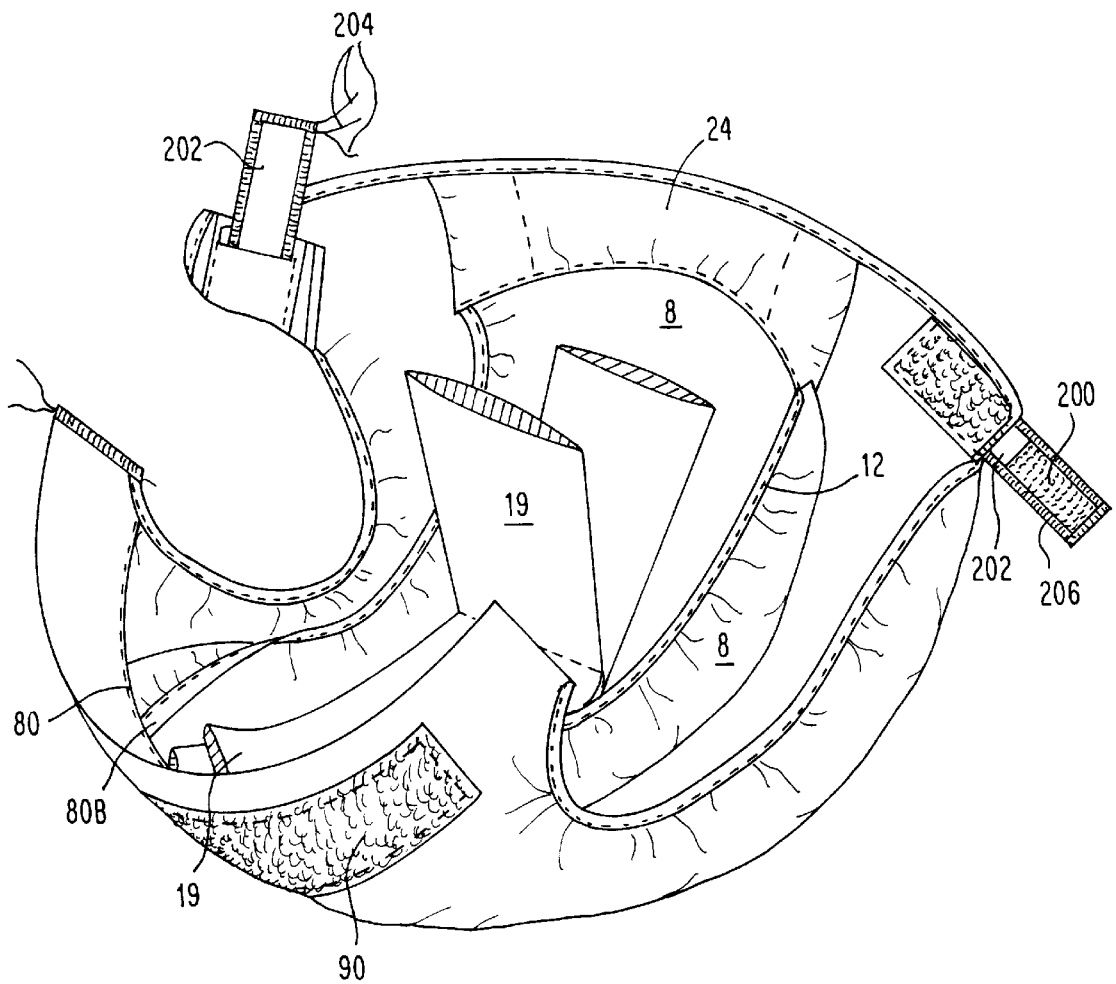
FIG. 13 is a view of a sling device, whereby the frontal sling sides of the end turned inward to form a pocket to receive a pad.
Figure 13A:
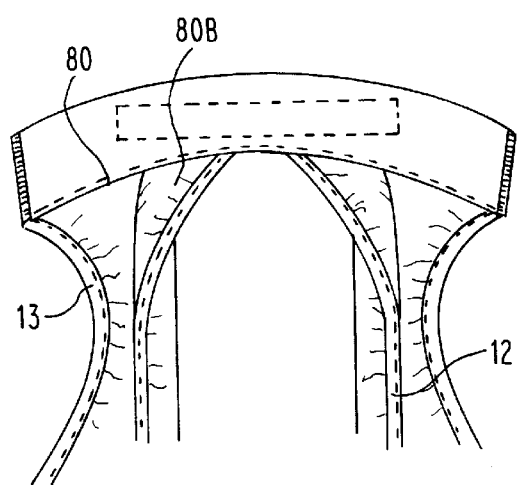

FIG. 13 shows an additional diaper embodiment of simplified yet highly efficient sling design with its formed pocket 80B construction. Sling 8, as in previous embodiments is now devoid of its sewn pad and drop strips and is conformed to contain a pad by turning frontal end of corners of said sling 8, inward to central portion of said sling at sealing line 80 to form pocket 80B which will retain a pad from slipping forward or sideward. Pad 19 advantageously retains fluid and the roll of the sides of sling keeps moisture in.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

I claim:

1. A tailored diaper, comprising:
   a fluid resistant diaper shell having inner and outer surfaces; and
   an elongated sling of material having upper and lower ends that are attached to, and opposite sides that are free and floating on, the inner surface of said shell;
   the ends of the opposite sides of said sling, at least at one end of said diaper, being folded inward toward and secured at a center region of said sling, and the remainder of said opposite sides of said sling remaining unfolded, said inwardly folded ends of said sling establishing a pocket to entrap fluid and receive and restrain a removable fluid absorbent pad insert from forward or lateral slippage.

2. The diaper of claim 1, including, retained in said pocket of said sling, a removable fluid absorbent pad insert.

3. The diaper of claim 2, wherein the pad insert is comprised of multiple layers of fluid absorbent material, interconnected along a joining line to produce plural layers each extending from said joining line and terminating at a free end for presenting oppositely facing evaporation surfaces.

4. The diaper of claim 3, wherein the multiple layers of said pad are joined along a stitch line.

5. The diaper of claim 3, wherein the joining line bisects said pad laterally.

6. The diaper of claim 3, wherein the joining line bisects said pad longitudinally.

7. The diaper of claim 1, wherein the opposite sides of said shell are covered with an elastic strip.

8. The diaper of claim 1, wherein the folded opposite sides of said sling are stitched to said shell.

9. The diaper of claim 8, wherein the sling is stitched to said shell beneath a connecting piece of fluid resistant fabric.

10. The diaper of claim 9, wherein the sling and connecting piece are stitched together along an arcuate stitch line.

11. A garment, comprising:
    a piece of material having front and rear surfaces;
    first fastener tabs of filamentary material extending from opposite corners at one end of said piece of material;
    a second fastener tab of filamentary material positioned on the outer surface of said piece of material to couple to said first fastener tabs when the garment is worn;
    each said first fastener tab comprising:
      a first strip having a surface of hook type filamentary material;
      a second strip having a surface of loop type filamentary material;
      the first and second strips aligned back to back with each other and with the hook and loop type filamentary materials facing outward; and
      opposite side edges of said strips being covered by overlook stitching.

12. The garment of claim 11, wherein the first strip of hook type filamentary material has a length that is less than that of the second strip of loop type filamentary material so as to establish a hinge in a region of the tab comprising only the second strip, and the end of each said first fastener tab, adjacent said hinge, is attached to said piece of material.

* * * * *